United States Patent
Kato et al.

(10) Patent No.: US 9,295,262 B2
(45) Date of Patent: Mar. 29, 2016

(54) CHLORINE DIOXIDE-GENERATING PRODUCT AND METHOD FOR GENERATING CHLORINE DIOXIDE

(75) Inventors: Ryo Kato, Osaka (JP); Kanefusa Hara, Osaka (JP); Masanori Yanagida, Osaka (JP)

(73) Assignee: OSAKA SODA CO., LTD., Osaka (JP)

( * ) Notice: Subject to any disclaimer, the term of this patent is extended or adjusted under 35 U.S.C. 154(b) by 107 days.

(21) Appl. No.: 14/122,554

(22) PCT Filed: May 30, 2012

(86) PCT No.: PCT/JP2012/063897
§ 371 (c)(1),
(2), (4) Date: Jan. 3, 2014

(87) PCT Pub. No.: WO2012/165466
PCT Pub. Date: Dec. 6, 2012

(65) Prior Publication Data
US 2014/0113007 A1    Apr. 24, 2014

(30) Foreign Application Priority Data

May 31, 2011   (JP) .................................. 2011-121635

(51) Int. Cl.
*C01B 11/02* (2006.01)
*A01N 59/08* (2006.01)
*A01N 59/00* (2006.01)

(52) U.S. Cl.
CPC ................ *A01N 59/08* (2013.01); *A01N 59/00* (2013.01); *C01B 11/024* (2013.01)

(58) Field of Classification Search
USPC ................................................. 423/477, 478
See application file for complete search history.

(56) References Cited

U.S. PATENT DOCUMENTS

| | | | |
|---|---|---|---|
| 4,547,381 A | 10/1985 | Mason et al. | |
| 5,110,580 A * | 5/1992 | Rosenblatt | C01B 11/024 252/187.23 |
| 5,234,678 A * | 8/1993 | Rosenblatt | C01B 11/024 422/37 |
| 6,174,508 B1 | 1/2001 | Klatte | |
| 6,432,322 B1 | 8/2002 | Speronello et al. | |
| 6,555,053 B1 | 4/2003 | Aoyagi | |
| 7,150,854 B2 * | 12/2006 | Koermer | C01B 11/024 252/175 |
| 2003/0080317 A1 | 5/2003 | Speronello et al. | |
| 2003/0180384 A1 | 9/2003 | Koermer et al. | |
| 2004/0135116 A1 | 7/2004 | Speronello et al. | |
| 2006/0039840 A1 | 2/2006 | Chia et al. | |
| 2006/0169949 A1 | 8/2006 | Speronello et al. | |
| 2007/0081919 A1 | 4/2007 | Koermer et al. | |
| 2008/0131395 A1 * | 6/2008 | Wellinghoff | A01N 25/10 424/76.3 |

FOREIGN PATENT DOCUMENTS

| | | |
|---|---|---|
| CN | 102835421 A * | 12/2012 |
| JP | S61-181532 A | 8/1986 |
| JP | 02055201 | 2/1990 |
| JP | H11-278808 A | 10/1999 |
| JP | 2000202009 A | 7/2000 |
| JP | 2005520769 A | 7/2005 |
| JP | 2007001807 A | 1/2007 |
| JP | 2009-185043 A | 8/2009 |
| WO | WO-9962817 A1 | 12/1999 |

OTHER PUBLICATIONS

International Preliminary Report on Patentability for International application No. PCT/JP012/063897, dated Dec. 2, 2013.
Written Opinion for International application No. PCT/JP012/063897, dated Dec. 2, 2013.
International Search Report in corresponding PCT/JP2012/063897 dated Jul. 3, 2012.
Written Opinion in corresponding PCT/JP2012/063897 dated Jul. 3, 2012.
Extended European Search Report in corresponding PCT/JP2012/063897 dated Oct. 14, 2014.

* cited by examiner

*Primary Examiner* — James McDonough
(74) *Attorney, Agent, or Firm* — Marshall, Gerstein & Borun LLP

(57) ABSTRACT

Provided is a chlorine dioxide-generating product comprising an inorganic porous carrier carrying a chlorite and an alkali agent. In the product, the alkali agent is carried in an amount of more than 0.7 molar equivalent and not more than 2 molar equivalents relative to the amount of the chlorite carried, and the product has a water content of 10% by weight or less. The chlorine dioxide-generating product can stably generate chlorine dioxide gas in an amount that sufficiently achieves deodorization, sterilization, virus removal, mold prevention, antisepsis, or the like of spatial environments, foods, or others but exerts no harmful effect on humans, over a long period of time.

11 Claims, No Drawings

CHLORINE DIOXIDE-GENERATING PRODUCT AND METHOD FOR GENERATING CHLORINE DIOXIDE

TECHNICAL FIELD

The present invention relates to a chlorine dioxide-generating product used for deodorization, sterilization, virus removal, mold prevention, antisepsis, or other purposes of spatial environments or foods and a method for stably generating a dilute chlorine dioxide gas using the product.

BACKGROUND ART

Chlorine dioxide, which has high oxidizing power, looks promising for applications including deodorization, sterilization, virus removal, mold prevention, antisepsis, and bleaching. However, the chlorine dioxide is extremely unstable and is unsuitable for long-term storage or conveyance. In addition, chlorine dioxide in high concentration involves a risk of explosion. In order to solve these problems, various methods have been proposed.

A gel composition comprising chlorine dioxide and a water-absorbing resin has been developed (for example, see Patent Literature 1), but the composition generates little chlorine dioxide gas. In order to solve the problem, a method of irradiating a gel composition comprising chlorine dioxide and a water-absorbing resin with ultraviolet light has been proposed (for example, see Patent Literature 2), but the method requires a combined ultraviolet irradiation apparatus.

A gel composition comprising a pure chlorine dioxide-generating product containing dissolved chlorine dioxide gas, a chlorite, and a pH adjuster for maintaining the product acidic and a high water-absorbing resin has been developed (for example, see Patent Literature 3), but it is unsuitable for long-term storage due to the degradation of the dissolved chlorine dioxide.

A method of adding an activator, a water-absorbing resin, and a water-retaining agent to an aqueous chlorite solution and converting the mixture into a gel has been developed (for example, see Patent Literature 4). However, the method requires the addition of the agents just before use. In addition, the method fails to control the reaction after the addition of the agents and generates chlorine dioxide gas at high concentration for several days. The method accordingly has problems concerning handling safety issues and concentration control.

CITATION LIST

Patent Literature

[Patent Literature 1] Japanese Patent Application Publication No. 61-181532
[Patent Literature 2] Japanese Patent Application Publication No. 2000-202009
[Patent Literature 3] Japanese Patent Application Publication No. 11-278808
[Patent Literature 4] Japanese Patent Application Publication No. 2007-1807

SUMMARY OF INVENTION

Technical Problem

The present invention has an object to provide a chlorine dioxide-generating product that stably generates chlorine dioxide in an appropriate amount for the deodorization, sterilization, virus removal, mold prevention, antisepsis, or the like of spatial environments or foods and to provide a method that suppresses the generation of chlorine dioxide until use and efficiently generates chlorine dioxide at the time of use.

Solution to Problem

As a result of repeated studies to solve the problems, the inventors of the present invention have obtained the following findings:

(i) A chlorine dioxide-generating product comprising an inorganic porous carrier carrying a chlorite and an alkali agent, the alkali agent being carried in an amount of more than 0.7 molar equivalent and not more than 2 molar equivalents relative to the amount of the chlorite carried, the product having a water content of 10% by weight or less, can stably generate chlorine dioxide in an amount that sufficiently achieves deodorization, sterilization, virus removal, mold prevention, antisepsis, or the like of open spaces, foods, or others but exerts no harmful effect on humans or animals, over a long period of time.

(ii) By preventing a chlorine dioxide-generating product from coming in contact with carbon dioxide and/or water vapor until use and bringing the chlorine dioxide-generating product into contact with a gas containing carbon dioxide and water vapor, an acid, or an oxidative substance at the time of use, suppression of the generation of useless chlorine dioxide and efficient generation of chlorine dioxide at the time of use can be achieved.

The present invention has been completed based on the above findings and provides the chlorine dioxide-generating products and the methods for generating chlorine dioxide shown below.

[1] A chlorine dioxide-generating product comprising an inorganic porous carrier carrying a chlorite and an alkali agent,
the alkali agent being carried in an amount of more than 0.7 molar equivalent and not more than 2 molar equivalents relative to the amount of the chlorite carried,
the chlorine dioxide-generating product having a water content of 10% by weight or less.
[2] The chlorine dioxide-generating product according to the above [1] obtained by infiltrating the chlorite and the alkali agent into the inorganic porous carrier and drying the carrier.
[3] The chlorine dioxide-generating product according to the above [2], wherein the chlorite and the alkali agent are infiltrated into the inorganic porous carrier by spraying.
[4] The chlorine dioxide-generating product according to any one of the above [1] to [3], wherein the chlorite is carried in an amount of 1 to 25% by weight relative to the total amount of the chlorine dioxide-generating product.
[5] The chlorine dioxide-generating product according to any one of the above [1] to [3], wherein the chlorite is carried in an amount of 1 to 40 parts by weight relative to 100 parts by weight of the inorganic porous carrier.
[6] The chlorine dioxide-generating product according to any one of the above [2] to [5], wherein 10 to 100 parts by weight of a solution containing the chlorite at a concentration of 1 to 46% by weight and the alkali agent at a concentration of 1 to 60% by weight is infiltrated into 100 parts by weight of the inorganic porous carrier.
[7] The chlorine dioxide-generating product according to any one of the above [1] to [6], of which the inorganic porous carrier, when suspended at a concentration of 10% by weight in water, gives an alkaline suspension.

[8] The chlorine dioxide-generating product according to any one of the above [1] to [7], wherein the inorganic porous carrier is palygorskite or sepiolite.
[9] The chlorine dioxide-generating product according to any one of the above [1] to [8] having a water content of 5% by weight or less.
[10] A method for generating chlorine dioxide, the method comprising:
preventing a chlorine dioxide-generating product from coming in contact with carbon dioxide and/or water vapor until use; and
bringing the chlorine dioxide-generating product into contact with a gas containing carbon dioxide and water vapor, an acid, or an oxidative substance to generate chlorine dioxide at the time of use.
[11] The method according to the above [10], wherein the chlorine dioxide-generating product is blocked from coming in contact with carbon dioxide and water vapor until use and the chlorine dioxide-generating product is brought into contact with air at the time of use.
[12] The method according to the above [10] or [11], wherein the chlorine dioxide-generating product is the chlorine dioxide-generating product according to any one of the above [1] to [9].

Advantageous Effects of Invention

A chlorine dioxide-generating product of the present invention can stably generate chlorine dioxide gas in an amount sufficient to achieve deodorization, sterilization, virus removal, mold prevention, antisepsis, or the like of open spaces, foods, or others and in an amount to exert no harmful effect on humans or animals, over a long period of time.

A method of the present invention suppresses the generation of chlorine dioxide during, for example, storage or distribution, and thus is suitable for long-term storage or conveyance, reduces the risk of explosion, and can suppress the effect on humans or animals except during use. In addition, the method can efficiently generate chlorine dioxide at the time of use.

DESCRIPTION OF EMBODIMENTS

Embodiments for carrying out the present invention will be described hereinbelow.
(I) Chlorine Dioxide-Generating Product
A chlorine dioxide-generating product in the present invention is a substance generating or releasing chlorine dioxide.
Inorganic Porous Carrier
The type of an inorganic porous carrier is not particularly limited and any known inorganic porous carrier can be used without limitation. Examples of the known inorganic porous carrier include sepiolite, palygorskite, montmorillonite, silica gel, diatomaceous earth, zeolite, and pearlite. Among them, for suppression of the degradation of a chlorite, preferred are those whose suspensions at a concentration of 10% by weight in water are alkaline or have a pH of 8 or more. More preferred are palygorskite and sepiolite, and particularly preferred is sepiolite.
Sepiolite is a natural mineral of magnesium silicate and the structural formula of sepiolite is represented by the following general formula (1).

(1)

The crystal structure of sepiolite has a fibrous form, a large number of grooves on the surface, and a large number of cylindrical tunnel-structured clearances inside, and thus has a very large specific surface area. The present invention may employ any of a pulverized and purified product of a crude sepiolite ore, a molded product of a pulverized sepiolite, and a product obtained by heating and burning such a sepiolite product at about 100 to 800° C. The sepiolite may have any of a granular form, a powder form, a fibrous form, and a molded form thereof. Sepiolite has a very large water absorbing and holding capacity, and even after absorbing the same weight of water as that of the sepiolite itself, can have a substantially dry surface.

The form of the inorganic porous carrier is not particularly limited and may be any of a granular form, a powder form, a fibrous form, and a molded form thereof. Among them, a granular form is preferred.

The inorganic porous carrier in a granular form or a powder form preferably has an average particle size of about 0.1 to 10 mm, more preferably about 0.3 to 6 mm, and even more preferably about 0.5 to 3 mm. The average particle size is determined by the sieving test (JIS Z 8815).

The inorganic porous carrier preferably has a specific surface area of about 50 to 350 $m^2/g$, more preferably about 70 to 250 $m^2/g$, and even more preferably about 100 to 200 $m^2/g$. The specific surface area is determined by the multipoint BET method (JIS Z 8830).

The inorganic porous carrier preferably has a pore volume of about 0.1 to 0.7 cc/g, more preferably about 0.15 to 0.6 cc/g, and even more preferably about 0.2 to 0.5 cc/g. The pore volume is determined by the multipoint BET method (JIS Z 8830).
Chlorite
The chlorine dioxide-generating product of the present invention carries a chlorite and preferably, uniformly carries a chlorite.

Examples of the chlorite include alkali metal salts of chlorous acid, such as sodium chlorite, potassium chlorite, and lithium chlorite and alkaline earth metal salts such as magnesium chlorite and calcium chlorite. Among them, alkali metal salts are preferred and sodium chlorite is more preferred because such a compound is inexpensive and commercially available for general purposes.

The amount of the chlorite is preferably 1% by weight or more, more preferably 3% by weight or more, and even more preferably 5% by weight or more relative to the total amount of the chlorine dioxide-generating product. When the amount of the chlorite is in the range, the product can sufficiently generate chlorine dioxide. The amount of the chlorite is preferably 25% by weight or less and more preferably 20% by weight or less relative to the total amount of the chlorine dioxide-generating product. When the amount of the chlorite is in the range, the chlorine dioxide-generating product is not designated as the deleterious substances.

The amount of the chlorite is preferably 1 to 40 parts by weight, more preferably 3 to 25 parts by weight, and even more preferably 5 to 20 parts by weight, relative to 100 parts by weight of the inorganic porous carrier.
Alkali Agent
The chlorine dioxide-generating product of the present invention carries an alkali agent and preferably, uniformly carries an alkali agent.

Examples of the alkali agent include hydroxides such as sodium hydroxide, potassium hydroxide, and lithium hydroxide and carbonates such as sodium carbonate, potassium carbonate, and lithium carbonate. Among them, sodium hydroxide and sodium carbonate are preferred from the viewpoint of economic advantages, and sodium hydroxide is more preferred from the viewpoint of good storage stability of the chlorine dioxide-generating product.

The amount of the alkali agent is preferably more than 0.7 molar equivalent, more preferably 0.73 molar equivalent or more, and even more preferably 0.75 molar equivalent or more relative to the amount (mol) of the chlorite. When the amount of the alkali agent is in the range, the carried chlorite hardly degrades at ordinary temperature. In addition, such a product does not generate an excess amount of chlorine dioxide within a short period of time but can stably generate chlorine dioxide over a long period of time in such an amount that the chlorine dioxide can achieve disinfection or other effects.

The chlorine dioxide-generating product preferably carries an alkali agent in an amount of 2 molar equivalents or less relative to the amount (mol) of the chlorite. The amount is more preferably 1.7 molar equivalents or less and even more preferably 1.2 molar equivalents or less. When the amount of the alkali agent is in the range, the chlorine dioxide-generating product consistently generates chlorine dioxide. Such a chlorine dioxide-generating product is not designated as the hazardous materials or does not involve the risk of generating an excess amount of a chlorine dioxide gas.

Water Content

The performance of the chlorine dioxide-generating product of the present invention is largely affected by its water content. In other words, an excessively high water content of the chlorine dioxide-generating product accelerates the degradation of the chlorite into a chlorate. In addition, an excessively high water content reduces the amount of chlorine dioxide generated. For the reasons, the chlorine dioxide-generating product has a water content of 10% by weight or less, preferably 5% by weight or less, and more preferably 3% by weight or less. The chlorine dioxide-generating product most preferably contains no water.

Production Method

The method of causing an inorganic porous carrier to carry the chlorite and the alkali agent is not particularly limited. Examples of the method include impregnation and spraying. The spraying is preferred because an increased amount of chlorine dioxide can be generated or chlorine dioxide can be stably generated.

In the impregnation, the inorganic porous carrier in a dried state may be separately impregnated with a solution of the chlorite and a solution of the alkali agent or impregnated with a solution containing both the chlorite and the alkali agent. For the inorganic porous carrier uniformly carrying the components, the impregnation with the solution containing both the chlorite and the alkali agent is preferred. In the case of separate impregnation, the inorganic porous carrier may be first impregnated with either of the solutions, but is preferably impregnated with the alkali agent first.

In the spraying, the inorganic porous carrier in a dried state may be separately sprayed with a solution of the chlorite and a solution of the alkali agent or sprayed with a solution containing both the chlorite and the alkali agent. For the inorganic porous carrier uniformly carrying the components, the spraying with the solution containing both the chlorite and the alkali agent is preferred. In the case of separate spraying, the inorganic porous carrier may be first sprayed with either of the solutions, but is preferably impregnated with the alkali agent first.

The solution for impregnation or spraying is typically an aqueous solution but may contain an organic solvent as long as the solution can dissolve the chlorite and the alkali agent.

For the impregnation or the spraying of the solution containing the chlorite and the alkali agent, 100 parts by weight of the inorganic porous carrier may be impregnated or sprayed with 10 to 100 parts by weight of a solution containing the chlorite at a concentration of 1 to 46% by weight and the alkali agent at a concentration of 1 to 60% by weight.

In particular, 100 parts by weight of the inorganic porous carrier preferably carries the solution containing the chlorite at a concentration of 1 to 46% by weight and the alkali agent at a concentration of 1 to 60% by weight in a total amount of 70 parts by weight or less. Such a chlorine dioxide-generating product contains a chlorite but is not classified into the hazardous materials, Category I, Item (iii) under the current Fire Service Act, and this enables simpler and safer handling.

After the infiltration of the chlorite and the alkali agent to the inorganic porous carrier, the whole may be dried as necessary. The impregnation or the spraying and the drying may be repeated twice or more and this can increase the amounts of the chlorite and the alkali agent carried.

The drying method is not particularly limited but the drying can be performed with a vacuum dryer, a fluidized bed dryer, a shelf dryer, a rotary dryer, a reduced-pressure dryer, or other apparatuses. The drying condition is also not particularly limited, but the drying is performed at 30 to 150° C., preferably at 70 to 130° C. for 0.5 to 10 hours, preferably for 0.5 to 5 hours, for example.

(II) Method for Generating Chlorine Dioxide

The method for generating chlorine dioxide of the present invention is a method of preventing a chlorine dioxide-generating product from coming in contact with carbon dioxide and/or water vapor until use and bringing the chlorine dioxide-generating product into contact with a gas containing carbon dioxide and water vapor, an acid, or an oxidative substance to generate chlorine dioxide at the time of use.

For generation of a stable amount of chlorine dioxide over a long period of time, the chlorine dioxide-generating product is preferably brought into contact with air.

The contact with an acid or an oxidative substance can be performed by mixing the chlorine dioxide-generating product with the acid or the oxidative substance, for example.

Examples of the acid include strong acids such as hydrochloric acid, sulfuric acid, and nitric acid and weak acids such as formic acid, acetic acid, citric acid, and adipic acid. Examples of the oxidative substance include ozone and chlorine. For easy control of the amount of chlorine dioxide generated, acids are preferred and weak acids are specifically preferred. In particular, a method of mixing the chlorine dioxide-generating product with an acid in a solid form at an ordinary temperature (23° C.), such as citric acid and adipic acid, is preferred because the resulting mixture can absorb water in air to gradually release chlorine dioxide.

A method of bringing the chlorine dioxide-generating product into contact with a gas containing carbon dioxide and water vapor, for example, with air is also preferred because the method is simple and practical.

As described in Examples below, the inventors of the present invention have compared the amounts of chlorine dioxide generated in the following three cases: the case of passing air through the chlorine dioxide-generating product of the present invention; the case of passing air from which carbon dioxide is almost completely trapped (removed) with use of an aqueous sodium hydroxide solution; and the case of passing air from which carbon dioxide and water vapor are almost completely trapped (removed) with use of an aqueous sodium hydroxide solution and calcium chloride (see Table 4). In comparison with the case of passing air, the case of passing air from which carbon dioxide was trapped resulted in a large reduction in the amount of chlorine dioxide generated.

In addition, the case of passing air from which carbon dioxide and water vapor were trapped generated almost no chlorine dioxide.

When water vapor and carbon dioxide are absorbed into pores in the chlorine dioxide-generating product, carbonic acid is generated as shown in the general formula (2) below. Carbonic acid is a weak acid having a first dissociation constant pK1 of 6.4 and thus the carbonic acid is supposed to react as an acid with a chlorite to generate chlorine dioxide.

$$CO_2 + 2H_2O \rightarrow H_2CO_3 \qquad (2)$$

Hence, the chlorine dioxide-generating product is not required to be brought into contact with an acid or an oxidative substance, but bringing the product into contact with carbon dioxide and water vapor or simply bringing the product into contact with air allows the chlorine dioxide-generating product to react with carbonic acid generated in the air, and the reaction can generate chlorine dioxide. In other words, preventing the chlorine dioxide-generating product from coming in contact with carbon dioxide and/or water vapor, preferably with both, or preferably blocking the contact can suppress the generation of chlorine dioxide.

More specifically, when unused, for example, the product is stored in a container made of a material that is almost impermeable to carbon dioxide and/or water vapor or is packed with a wrapping material that is almost impermeable to carbon dioxide and/or water vapor, and this suppresses the generation of chlorine dioxide. At the time of use, the product is taken out of the container, the container is unsealed, or the wrapping material is removed, and as a result the product comes in contact with outside air for the first time, thereby gradually generating a chlorine dioxide gas. Alternatively, an absorber for water content and/or carbon dioxide may be set in a container or a wrapping material, and at the time of use, the chlorine dioxide-generating product can be taken out of the container or the wrapping material to come in contact with air.

In order to prevent the contact with carbon dioxide when unused, the chlorine dioxide-generating product is packed with a container or a packing material preferably having a carbon dioxide permeability of $2.5 \times 10^{-11}$ cc (STP)/$cm^2 \cdot sec \cdot cmHg$ or less and more preferably $5 \times 10^{-10}$ cc (STP) $mm/cm^2 \cdot sec \cdot cmHg$ or less. In particular, the product is preferably packed with a container or a packing material having a carbon dioxide permeability of $5 \times 10^{-10}$ cc (STP) $mm/cm^2 \cdot sec \cdot cmHg$ or less in the case of a film having a thickness of 50 μm.

In order to prevent the contact with carbon dioxide when unused, the chlorine dioxide-generating product is packed with a container or a packing material preferably having a water vapor permeability of $5 \times 10^{-9}$ cc (STP)/$cm^2 \cdot sec \cdot cmHg$ or less and more preferably $1,000 \times 10^{-10}$ cc (STP) $mm/cm^2 \cdot sec \cdot cmHg$ or less. In particular, the product is preferably packed with a container or a packing material having a water vapor permeability of $1,000 \times 10^{-10}$ cc (STP) $mm/cm^2 \cdot sec \cdot cmHg$ or less in the case of a film having a thickness of 50 μm.

Metal or glass is also a material that is almost impermeable to carbon dioxide or water vapor, but the wrapping material or an inner lid of the container is commonly made of a plastic film. Examples of the plastic include aluminum-deposited polyethylene (specifically, an aluminum-deposited polyethylene film), vinylidene chloride, and polychlorotrifluoroethylene.

The chlorine dioxide-generating product used in the method of the present invention is not particularly limited, and may be a product containing a chlorite and an alkali agent and capable of releasing chlorine dioxide. The chlorine dioxide-generating product preferably has a water content of 10% by weight or less, more preferably 5% by weight or less, and even more preferably 3% by weight or less. The chlorine dioxide-generating product preferably carries the alkali agent in an amount of 2 molar equivalents or less, more preferably 1.7 molar equivalents or less, and even more preferably 1.2 molar equivalents or less, relative to the amount (mol) of the chlorite. The chlorine dioxide-generating product preferably carries the alkali agent in an amount of more than 0.7 molar equivalent, more preferably more than 0.73 molar equivalent, and even more preferably more than 0.75 molar equivalent, relative to the amount (mol) of the chlorite. The chlorite and the alkali agent may be those exemplified for the chlorine dioxide-generating product of the present invention above. The chlorine dioxide-generating product in the method of the present invention is specifically, preferably the chlorine dioxide-generating product of the present invention described above.

EXAMPLES

The present invention will now be described in more detail with reference to Examples and Comparative Examples.
Chlorine Dioxide Gas Generation Test An aqueous solution of 25% by weight of sodium chlorite and an aqueous solution of 25% by weight of sodium hydroxide were mixed in a predetermined ratio to prepare a solution, and 70 parts by weight of the solution was sprayed and infiltrated into 100 parts by weight of sepiolite ("Miraclay G-13F" (particle size: 1 to 3 mm) or "Miraclay G1630F" (particle size: 0.5 to 1 mm) manufactured by Omi Mining Co., Ltd.) that had been burned at around 700° C. for 25 hours and then cooled. The whole was dried under vacuum at 70° C. for 2 hours to give chlorine dioxide-generating products A to I having compositions shown in Table 1.

The water content was determined with a moisture meter (MX-50 manufactured by A&D Company, Limited, preset temperature: 130° C.)

TABLE 1

| | NaClO$_2$ (wt %) | NaOH*[1] (wt %) | Water (wt %) | Sepiolite (wt %) |
|---|---|---|---|---|
| A (Example 1) *[2] | 8.0 | 3.5 (1.06) | 3.0 | 85.5 |
| B (Example 2) *[2] | 9.0 | 3.0 (0.75) | 3.0 | 85.0 |
| C (Example 3) *[3] | 9.0 | 3.0 (0.75) | 3.0 | 85.0 |
| D (Example 4) *[3] | 6.0 | 6.0 (1.68) | 3.0 | 85.0 |
| E (Comparative Example 1) *[3] | 9.0 | 2.0 (0.50) | 3.0 | 85.0 |
| F (Comparative Example 2) *[3] | 10.0 | 1.5 (0.34) | 3.0 | 85.5 |
| G (Comparative Example 3) *[3] | 11.0 | 1.0 (0.21) | 3.0 | 85.0 |
| H (Comparative Example 4) *[3] | 3.0 | 9.0 (2.53) | 3.0 | 85.0 |
| I (Comparative Example 5) *[3] | 8.1 | 2.7 (0.75) | 14.2 | 75.0 |

*[1] The number in parentheses represents the molar equivalent of NaOH relative to NaClO$_2$.
*[2] Examples 1 and 2 employed Miraclay G-13F.
*[3] Examples 3 and 4 and Comparative Examples 1 to 5 employed Miraclay G1630F.

In a glass sample bottle (volume: 30 mL), 8 g of each of the chlorine dioxide-generating products A to C, E to G, and I was placed. The bottle was sealed and left at a temperature of 40° C. and a humidity of 75% for 2 months. Then the concentration of sodium chlorite in each chlorine dioxide-generating product was determined by an iodometric titration method. Specifically, 0.2 g of the chlorine dioxide-generating product in the sample bottle was weighed out and suspended in 20 mL of distilled water. Distilled water was further added to make 100 mL of solution. To the solution, 0.5 g of potassium iodide and 3 mL of 2.3M hydrochloric acid were added, and the mixture was titrated with 0.1M sodium thiosulfate solution to determine the chlorous acid concentration.

Table 2 shows the results.

TABLE 2

|   | Before storage (wt %) | After storage (wt %) |
|---|---|---|
| A (Example 1) | 8.0 | 8.0 |
| B (Example 2) | 9.0 | 9.0 |
| C (Example 3) | 9.0 | 8.0 |
| E (Comparative Example 1) | 9.0 | 5.8 |
| F (Comparative Example 2) | 10.0 | 4.2 |
| G (Comparative Example 3) | 11.0 | 3.9 |
| I (Comparative Example 4) | 8.0 | 7.6 |

The chlorine dioxide-generating products E (Comparative Example 1), F (Comparative Example 2), and G (Comparative Example 3) that carried the alkali agent in an amount of 0.7 molar equivalent or less relative to chlorous acid resulted in a large reduction in the amount of chlorine dioxide generated after two months from the start of use. In contrast, the chlorine dioxide-generating products A to C (Examples 1 to 3) of the present invention resulted in a reduction in the amount of a chlorite generated by 10% or less in two months.

Next, 40 g of each of the chlorine dioxide-generating products A to I was packed in a 300-mL glass column (diameter: 50 mm, height: 150 mm). Then, air was passed through the column at 1 L/min for 2 hours at a temperature of 25° C. and a humidity of 60%, and the outlet gas was adsorbed in a potassium iodide solution that was adjusted with a phosphate buffer solution to have a pH of 7. The iodine released by the chlorine dioxide was titrated with a sodium thiosulfate solution to determine the amount of chlorine dioxide gas generated. Table 3 shows the results obtained. The unit is the amount mg/hr of chlorine dioxide gas generated per kg of chlorine dioxide-generating product.

TABLE 3

|   | Amount of chlorine dioxide gas generated (mg/hr · kg) |
|---|---|
| A (Example 1) | 5.0 |
| B (Example 2) | 5.0 |
| C (Example 3) | 5.0 |
| D (Example 4) | 5.0 |
| E (Comparative Example 1) | 17.0 |
| F (Comparative Example 2) | 15.0 |
| G (Comparative Example 3) | 29.0 |
| H (Comparative Example 4) | 0.1 |
| I (Comparative Example 5) | 1.0 |

Under the accelerated condition of passing air, the chlorine dioxide-generating products E (Comparative Example 1), F (Comparative Example 2), and G (Comparative Example 3) that carried the alkali agent in an amount of 0.7 molar equivalent or less relative to chlorous acid generated an excess amount of chlorine dioxide.

The chlorine dioxide-generating product H (Comparative Example 4) that carried an alkali agent in an amount of more than 2 molar equivalents relative to chlorous acid and the chlorine dioxide-generating product I (Comparative Example 5) that had a water content of more than 10% by weight generated little chlorine dioxide gas even under the accelerated condition.

In contrast, the chlorine dioxide-generating products A to D (Examples 1 to 4) of the present invention generated an appropriate amount of chlorine dioxide gas.

The chlorine dioxide-generating products A to D of the present invention were able to stably generate an appropriate amount of chlorine dioxide gas over a long period of time as compared with the chlorine dioxide-generating products E to I.

Suppression Test of Chlorine Dioxide Gas Generation

In a 300-mL glass column (diameter: 50 mm, height: 150 mm), 40 g of the chlorine dioxide-generating product prepared in accordance with the composition C (Example 3) in Table 1 described above was packed. The amounts of chlorine dioxide generated at a temperature of 25° C. and a humidity of 60% in the following three cases were determined in a similar manner to that in the above:

Case 1 of passing common air at 1 L/min for 5 hours;

Case 2 of passing air from which carbon dioxide was almost completely blocked (trapped) by passing the air through 100 mL aqueous solution of 25% by weight of sodium hydroxide; and Case 3 of passing air from which carbon dioxide and water vapor were almost completely blocked (trapped) by passing the air through 100 mL aqueous solution of 25% by weight of sodium hydroxide and through a tube containing 200 g of calcium chloride.

Table 4 shows the results.

TABLE 4

|   | Case 1 | Case 2 | Case 3 |
|---|---|---|---|
| Amount of gas generated (mg/hr · kg) | 6.0 | 3.0 | 0 |

In comparison with Case 1 of passing common air, Case 2 of passing air from which carbon dioxide was almost completely blocked resulted in a large reduction in the amount of chlorine dioxide generated. Case 3 of passing air from which carbon dioxide and water vapor were almost completely blocked generated substantially no chlorine dioxide.

INDUSTRIAL APPLICABILITY

The chlorine dioxide-generating product of the present invention can stably generate chlorine dioxide in an appropriate amount over a long period of time and thus can be suitably used as a bactericide, a deodorant, an antiseptic, a fungicide, an antiviral agent, a bleach, or other agents.

The invention claimed is:

1. A chlorine dioxide-generating product comprising an inorganic porous carrier carrying a chlorite and sodium hydroxide, the sodium hydroxide being carried in an amount of more than 0.7 molar equivalent and not more than 2 molar equivalents relative to the amount of the chlorite carried, the chlorine dioxide-generating product having a water content of 10% by weight or less.

2. The chlorine dioxide-generating product according to claim 1, obtained by infiltrating the chlorite and the sodium hydroxide into the inorganic porous carrier and drying the carrier.

3. The chlorine dioxide-generating product according to claim 2, wherein the chlorite and the sodium hydroxide are infiltrated into the inorganic porous carrier by spraying.

4. The chlorine dioxide-generating product according to claim 1, wherein the chlorite is carried in an amount of 1 to 25% by weight relative to the total amount of the chlorine dioxide-generating product.

5. The chlorine dioxide-generating product according to claim 1, wherein the chlorite is carried in an amount of 1 to 40 parts by weight relative to 100 parts by weight of the inorganic porous carrier.

6. The chlorine dioxide-generating product according to claim 2, wherein 10 to 100 parts by weight of a solution containing the chlorite at a concentration of 1 to 46% by weight and the sodium hydroxide at a concentration of 1 to 60% by weight is infiltrated to 100 parts by weight of the inorganic porous carrier.

7. The chlorine dioxide-generating product according to claim 1, of which the inorganic porous carrier, when suspended at a concentration of 10% by weight in water, gives an alkaline suspension.

8. The chlorine dioxide-generating product according to claim 1, wherein the inorganic porous carrier is palygorskite or sepiolite.

9. The chlorine dioxide-generating product according to claim 1 having a water content of 5% by weight or less.

10. A method for generating chlorine dioxide, the method comprising:
   preventing a chlorine dioxide-generating product defined as claim 1 from coming in contact with carbon dioxide and/or water vapor until use; and
   bringing the chlorine dioxide-generating product into contact with a gas containing carbon dioxide and water vapor, an acid, or an oxidative substance to generate chlorine dioxide at the time of use.

11. The method according to claim 10, wherein the chlorine dioxide-generating product is blocked from coming in contact with carbon dioxide and water vapor until use and the chlorine dioxide-generating product is brought into contact with air at the time of use.

\* \* \* \* \*